US009089563B2

(12) United States Patent
Roseman

(10) Patent No.: US 9,089,563 B2
(45) Date of Patent: Jul. 28, 2015

(54) METHOD OF TREATING APRAXIA OF SPEECH IN CHILDREN

(75) Inventor: Bruce Roseman, White Plains, NY (US)

(73) Assignee: GILROSE PHARMACEUTICALS, LLC, White Plains, NY (US)

( * ) Notice: Subject to any disclaimer, the term of this patent is extended or adjusted under 35 U.S.C. 154(b) by 0 days.

(21) Appl. No.: 14/112,065

(22) PCT Filed: May 17, 2012

(86) PCT No.: PCT/US2012/038312
§ 371 (c)(1),
(2), (4) Date: Dec. 24, 2013

(87) PCT Pub. No.: WO2012/158892
PCT Pub. Date: Nov. 22, 2012

(65) Prior Publication Data
US 2014/0100247 A1    Apr. 10, 2014

Related U.S. Application Data

(60) Provisional application No. 61/487,847, filed on May 19, 2011.

(51) Int. Cl.
*A61K 31/435* (2006.01)
*A61K 31/4458* (2006.01)
*A61K 31/137* (2006.01)

(52) U.S. Cl.
CPC ........... *A61K 31/4458* (2013.01); *A61K 31/137* (2013.01)

(58) Field of Classification Search
CPC .................... A61K 31/4458; A61K 31/137
USPC ................................. 514/277, 654
See application file for complete search history.

(56) References Cited

U.S. PATENT DOCUMENTS

| 5,213,553 | A  | 5/1993  | Light |
| 6,121,261 | A  | 9/2000  | Glatt et al. |
| 8,426,423 | B2 | 4/2013  | Jordan et al. |
| 8,883,815 | B2 | 11/2014 | Roseman |
| 2004/0092605 | A1 | 5/2004 | Jerussi et al. |
| 2006/0052428 | A1 | 3/2006 | Chez |
| 2006/0161218 | A1 | 7/2006 | Danilov |
| 2011/0178114 | A1 | 7/2011 | Aung-Din |

FOREIGN PATENT DOCUMENTS

CA          2342432 A1 *  9/2002

OTHER PUBLICATIONS

Fish et al., "Effect of Amphetamines on Speech Defects in the Mentally Retarded", California Medicine, vol. 96, No. 2, pp. 109-111 (1962).*
The Effect of Methylphenidate on the Verbal Productivity of Children with Cerebral Dysfunction, Ray O. Creager and Catharaine VanRiper, J Speech Hear Res 1967; 10; pp. 623-628, Kalamazoo Child Guidance Clinic, Kalamazoo, Michigan, American Speech-Language-Hearing Association.
Methylphenidate for Giggle Incontinence, The Journal of Urology, Berry, Zderic, Carr, published online Aug. 20, 2009, www.jurology.com.
Methylpenidate for the Treatment of Gait Impairment in Parkinson's Disease, ClinicalTrials.gov, Sep. 5, 2007.
PCT/US2012/038312, International Search Report and Written Opinion, mailed Nov. 7, 2012, 5 pages.
Reorganization after pre-and perinatal Brain Lesions; Martin Staudt; Journal of Anatomy; 2010; pp. 469-474.
New insights into the pathology of white matter tracts in cerebral palsy . . . ; Schecket al.;Developmental Medicine & Child Neurology; Mar. 2012; pp. 684-695.
Pharmacotherapy of Spasticity in Children with Cerebral Palsy; Verrotti et al; Elsevier, Inc. 2006; pp. 1-6.
Speech and Language Therapy for Children with Cerebral Palsy . . . US National Library of Medicine; Jul. 21, 2006; pp. 1-2.
Intensive Speech and Language Therapy for Older Children..Cerebral Palsy . . . ; Pennington et al.; Developmental Medicine & Child Neurology; Apr. 2009; pp. 337-344.
Dopamine Treatment in Children with Cerebral Palsy; Shaare Zedek Medical Center; NIH; May 2011; pp. 1-3.
Perceptual and Articulatory Changes in Speech Production . . . Maria I. Griogs, Ph.D., et al.; J. Med. Speech Language Pathol 2012; 18(4); pp. 46-53.
Speech Problems Affect More Than One in Two Children With Cerebral Palsy . . . A. Nordberg et al.;ACTA Paediatriaca; 2012; pp. 161-166.
Speech, Expressive Language, and Verbal Cognition . . . with Cerebral Palsy in Iceland; Developmental Medicine & Child Neurology; Jul. 2010; Solveig et al.; pp. 74-80.
Oromotor Variability in Children with Mild Spastic Cerebral Palsy . . . ; Journal of Neuroengineering and Rehabilitation; 2010; Chia-Ling Chen, et al.; pp. 1-10.
Oromotor Dysfunction and Communication Impairments in Children with Cerebral Palsy . . . ; Parkes, et al.; Developmental Medicine & Child Neurology; Jun. 2010; pp. 1113-1119.
Long-Term Survival for a Cohort of Adults with Cerebral Palsy; Hemming Ph.D., et al.; Developmental Medicine & Child Neurology; 2006; 48: pp. 90-95.
Development of the FOCUS, a Communication Outcome Measure for Preschool Children; Thomas-Stonell, et al. Developmental Medicine & Child Neurology; Jun. 2009; pp. 47-53.
Language and Motor Speech Skills in Children with Cerebral Palsy; Pirila, et al.; Journal of Communication Disorders 40: (2007); pp. 116-128.

(Continued)

*Primary Examiner* — Kevin E Weddington
(74) *Attorney, Agent, or Firm* — Marvin Feldman, Esq.; Lackenbach Siegel, LLP

(57) ABSTRACT

A therapeutic method for treating apraxia of speech in children. The child can also be diagnosed with autism, mental retardation, dyslexia. Verbal development stages and nonverbal development stages are tested and observed. If a child demonstrates at least 18 to 24 month development stage of either the verbal development or the non-verbal development, a therapeutic dosage of dopamine agonistic medicine is administered to the child in addition to speech therapy and language training.

9 Claims, 3 Drawing Sheets

(56) References Cited

OTHER PUBLICATIONS

Survival of Individuals with Cerebral Palsy Born in Victoria, Australia . . . ; Reid, et al.; Developmental Medicine & Child Neurology; Oct. 2011; pp. 353-360.

Factors Associated with Motor Speech Control in Children with Spastic Cerebral Palsy; Chia-Ling Chen, et al.; Chang Gung Medical Journal; vol. 33, No. 4; Jul.-Aug. 2010; pp. 415-423.

Intensive Speech and Language Therapy for Older Children with Cerebral Palsy: A Systems Approach; Penning, et al.; Developmental Medicine & Child Neurology; Apr. 2009; pp. 337-344.

Dysarthria Treatment; Chandramita Bora; Apr. 19, 2010; Buzzle; pp. 1-2.

Speech and Language Therapy for Children With CP Might Improve Their Communication Skills, but More Research is Needed; PubMed Health/NIH; John Wiley & Sons, Ltd. pub. Jul. 21, 2003.

NINDS Cerebral Palsy Information Page; NIH National Institute of Neurological Disorders and Stroke . . . Aug. 21, 2013.

WO 2012/158892 (Roseman et al.); Nov. 22, 2012; Abstract

International Search Report PCT/US2014/060868.

Written Opinion.

\* cited by examiner

METHOD OF TREATING APRAXIA OF SPEECH IN CHILDREN

CROSS-REFERENCES TO OTHER RELATED APPLICATIONS

This application claims the priority of the U.S. Provisional Patent Application Ser. No. 61/487,847, filed on May 19, 2011, the entirety of which is hereby incorporated by reference.

BACKGROUND OF THE INVENTION

1. Field of the Invention

The present invention relates to treatment of speech and language learning impairment in children; more particularly, the present invention provides a therapeutic treatment method in combination of dopamine-related medicine for language learning ability impaired children.

2. Description of the Related Art

Current clinic diagnoses for cerebral dysfunctions are generally categorized according to a child's behavioral symptoms. For example, Apraxia is characterized by loss of the ability to execute or carry out learned purposeful movements despite having the desire and the physical ability to perform the movements. Attention Deficit and Hyperactivity Disorder (ADHD) is characterized with the co-existence of attentional problems and hyperactivity. Mental retardation is a disorder characterized by significantly impaired cognitive functioning and deficits in two or more adaptive behaviors, generally with an Intelligence Quotient score under 70. But it is not caused by incoordination, sensory loss, or failure to comprehend simple commands. Aphasia is characterized as an inability to produce and/or comprehend language. Autism is a disorder of neural development characterized by impaired social interaction and communication, and by restricted and repetitive behaviors. Dyslexia is characterized broadly as a learning disability that impairs a person's fluency or comprehension accuracy in being able to read, and which can manifest itself as a difficulty with phonological awareness, phonological decoding, orthographic coding, auditory short-term memory, or rapid naming. The descriptions of each of these diseases are overlapping and ambiguous. Almost all of these diseases involve certain level of language learning impairment.

Due to the lack of systematic methods for differentiating the neuronal physiological causes of these abnormal symptoms and behaviors, many early childhood development problems may thus be miss-treated. Infants, toddlers, children and adolescents who have disorders with speech, sound production, vocabulary building, difficulty with understanding the spoken word, clarity of speech, word retrieval, organization, reading fluency, word decoding, reading comprehension may also possess similar behavior symptoms as those of mental retardation, autism, emotionally disturbed, dyslexia, laziness and stupidity. For example, an impairment that inhibits or delays a child's early language learning ability, such as failure to acquire consistency in sound production, vocalization of consonants, vowels by early infancy will prevent a child from the development of the child's intellectual comprehension of commands and intellectual capacity. This could lead to the subsequent lack of emotional and social interaction skills, leading to clinical diagnosis of autism. But this child may have a level of other normal brain functions, for example, the part of brain that allows for normal non-verbal development and thus has the potential to be restored with medical treatment.

However, current methods of therapeutic treatment are mostly focused on behavioral and physical therapies, or strictly focused on language training. These physical trainings alone may not be sufficient for these children with certain level of brain dysfunctions. Miss-treated children may miss their critical development and learning stages, resulting in permanent behavior impairment.

The two cerebral hemispheres in humans are structurally and functionally asymmetrical. It is well established that the right brain hemisphere sustains the functions necessary for survivals, such as visual-spatial and emotional abilities while language abilities such as grammar, vocabulary and literal meaning are typically lateralized to the left brain hemisphere. During growing up, the development of the two brain hemispheres may be differentially affected or impaired by combination of many random factors. However, the left and right brain hemispheres may compensate each other's functions to a certain level with the correct use of medicine and physical trainings. It is possible for a language learning ability impaired child with a level of normal development of non-verbal functions to be medically induced to establish the positive-feedback of language learning.

Thus methods are needed for characterizing the level of a normal development of a language learning impaired child; and the combined medical treatments based on the biochemistry of the brain functions provide a novel option in addition to physical therapy and language training alone.

ASPECTS AND SUMMARY OF THE INVENTION

The present application discloses a novel method that dissects the causes of a child's abnormal development problems into verbal and non-verbal development associated causes, and provides a therapeutic treatment that combines medical treatment in addition to physical and language training in children.

In one embodiment, children of age 2-12 having clinical symptoms of autisms, dyslexia, mental retardation, and other language learning disabilities are observed and tested on their verbal and non-verbal abilities. Children with verbal impairment but having a level of functional normal non-verbal capabilities are selected for medical treatment in combination of physical and language therapy.

In one aspect of an embodiment, the treatment is a dosage of Methylphenidate.

In another aspect of an embodiment, the treatment is a dosage of Dextroamphetamine.

In another aspect of an embodiment, the treatment is a dosage of Gabapentin.

In another aspect of an embodiment, language trainings simultaneously provided with the administering of the medicines.

The medical treatment with a dopamine agonist drug in combination with physical and language training induces the establishment of the necessary positive feedback mechanism in the brain for the child to further develop its whole potential.

The above and other aspects, features and advantages of the present invention will become apparent from the following description read in conjunction with the accompanying drawings, in which like reference numerals designate the same elements.

BRIEF DESCRIPTION OF THE DRAWINGS

The disclosed application will be described with reference to the accompanying drawings, which show important sample embodiments of the invention and which are incorporated in the specification hereof by reference, wherein.

DETAILED DESCRIPTION OF THE PREFERRED EMBODIMENTS

Figure 1:
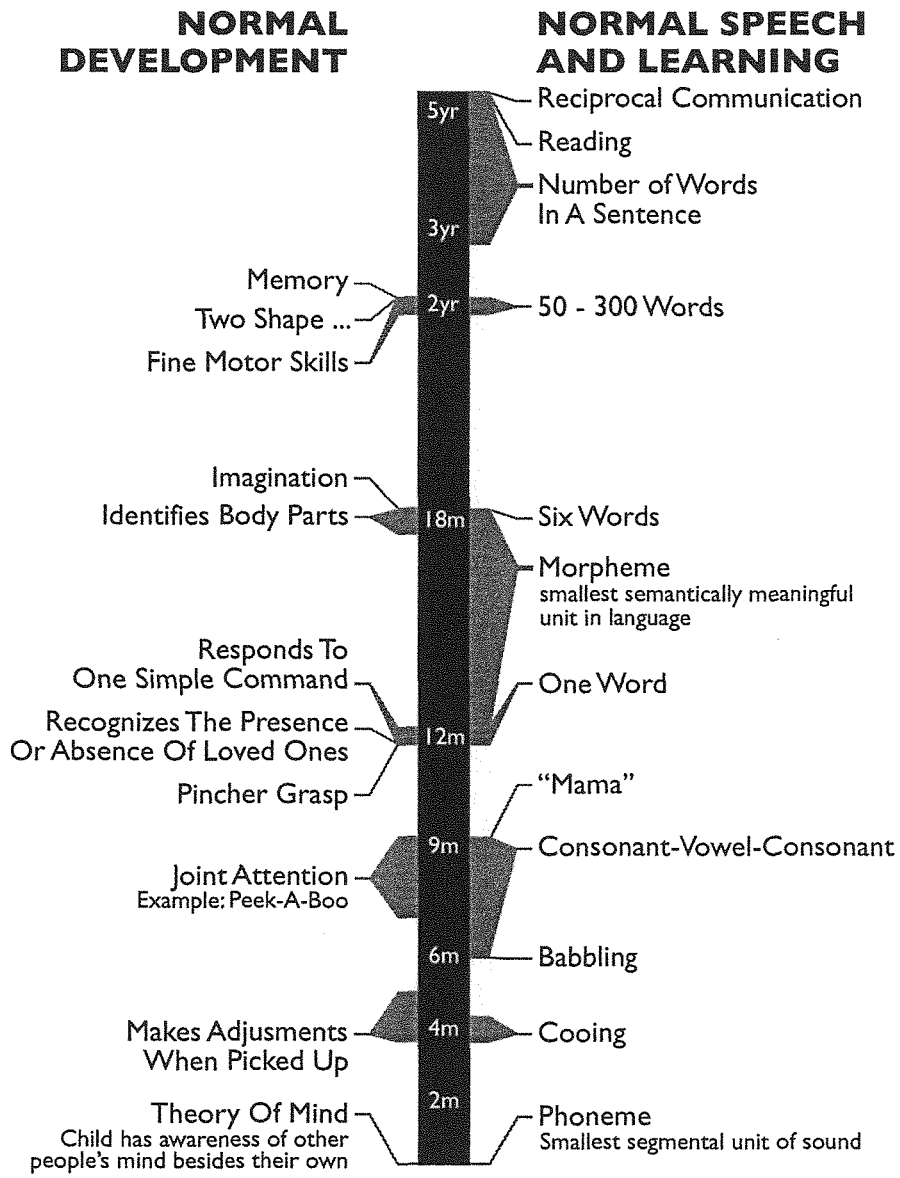
FIG. 1 is a graph of the parallel verbal and non-verbal developmental stages in a normal child.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

The terms "first," "second," "third," "fourth," and the like in the description and the claims, if any, may be used for distinguishing between similar elements and not necessarily for describing a particular sequential or chronological order. It is to be understood that the terms so used are interchangeable. Furthermore, the terms "comprise," "include," "have," and any variations thereof, are intended to cover non-exclusive inclusions, such that a process, method, article, apparatus, or composition that comprises a list of elements is not necessarily limited to those elements, but may include other elements not expressly listed or inherent to such process, method, article, apparatus, or composition.

Early childhood language learning impairment will not only interfere the child's ability to develop a working vocabulary of the mind to be present at least by 2 years of age in order to understand what other are saying, but also the ability of the child to call upon specific words in response to specific questions. As a result, many of these children by the time of 2 years of age show symptoms of autism.

Apraxia used herein is defined broadly as the breakdown of motor planning and execution at the super segmental level of the central nervous system in the presence of normal or subnormal motor and sensory functions. Speech apraxia in the pediatric population demonstrates symptoms of speech delay, problems in word recall, word sequencing, unintelligible speech, auditory processing, dyslexia. The present invention is directed towards treatment methods of apraxia of speech conditions in children younger than about 12 years old. The children may also be clinically diagnosed with other disorders, such as dyslexia, autism, mental retardations, or certain chromosome defects.

The method mainly comprises identifying an apraxia child patient who demonstrates a certain level of normal development of non-verbal functions, in addition to physical and language training, and also providing a medical treatment of a form of dopamine agonist drugs, such as methylphenidate (MPH), Dextroamphetamine (Dexedrine), or Gabapentin.

Human speech production, more importantly, consistency in sound production, depends on the sequencing, timing coordination of neural impulses under the direction of the frontal cortex. The frontal cortex is responsible for controlling the lung to send a defined volume of air, travelling at a specific velocity, resulting in vibration of the vocal cords. The transformation of this volume of air speeding into an acoustical sound is further shaped upon entering the oral pharynx where a specific change in the muscles of the oropharynx interacting with the fixed anatomy of the teeth, gums, etc. refines the sound into specific words.

It is the ability to be consistent in sound production that allows humans to use words, to understand others, and to be understood by others, to organize a dictionary of words/sounds in the human minds, to learn to read, to decode novel words by segmentation, and to understand novel printed words by having instant access to a well organized dictionary of sounds, of words.

Apraxia of speech in children may be related to many categories of diseases, causing delayed or under-development of human intelligence. For example, the inability to develop vocabulary and meaningful communication may cause a child to be socially isolated and be diagnosed as autism, mental retardation or dyslexia, etc.

Apraxia of speech in children therefore causes disorder of cognition, reduces the child's potential intellectual development, depriving them of their ability to speak, use words, make their wants known, reciprocally communicate to others. Because of the lack of positive-feedback to these children, they will appear to have more severe degenerative diseases.

Simply, the child who never develops clear speech will be diagnosed by his worst symptom. More than likely these children become disconnected from others because others are no longer aware to use gestures with joint attention, with pictures to visually communicate after most if not all of these children turn 2 years or older. What the child thought he heard himself saying or thinking he said is not what others heard or perceived. Soon the child is diagnosed as being part of autistic spectrum of disorder.

Novel application of stimulant medication to treat apraxia of speech in children, such as use of methylphenidate and dextroamphetamine, therefore is inclusive of any and all part of the apraxia pyramid independent of any and all associated medical disorders including autism, mental retardation and cognitive impairment.

A stimulant medication, such as methylphenidate, Dexedrine, by physically playing a role in restoring neural connections, improving cognitive function, allows the normally functioning part of the brain to establish the base level of language learning needed for further learning ability development, establishing the positive-feedback mechanism in the brain for long term development and self-healing.

The apraxia-related disorders can be "mild" to "severe." For example, a subject suffering from an apraxia-related disorder may be able to speak intelligible or semi-intelligible words, but the order or sequence of the words or events depicted in the words may be disrupted. On the other end of the spectrum, the subject may be unable to form any intelligible sound such that verbal communication is difficult or impossible. As reflected in the child's inability to use language according to rules of language, failure to recognize there is an orderly sequence when people reciprocally communicate with each others. For example, of subject, verb, object, syntax, prosody of speech, stresses of words etc.

It has been established that the Broca region of the left brain hemisphere is largely responsible for the verbal related functions. And the right brain hemisphere is largely associated with non-verbal related functions.

In reference to FIG. 1, it shows the standard and accepted timeline of verbal and non-verbal development in infants and children and the timing of theory of mind. The left side shows the normal timeline of non-verbal development, and the right side shows the normal verbal development in early childhood.

For example, at 4 months old, a child is able to make cooing sounds; at 6 to 9 months old, a child is able to be babbling and chattering; at 9-12 months old, a child is able to make out consonant-vowel-consonant and a single word; at 18 months old, a child is able to make out six words; and at 2 years old, a child is able to make out 20-300 words. At 3 to 5 years old, a child is able to make a sentence of several words and capable of reading and reciprocal communication.

On the other hand, for the normal non-verbal development, a child from theory of mind of 0 month develops to make truncal and zaxial movements to adjust when picked up at 4 months; at 6-9 months age, a child is able to make joint attention such as peek-a-boo; at age 12 months old, a child is able to respond to one single command, recognize the presence or absence of loved ones and pincher grasps; the action becomes interactive; at 18 months old, a child is capable of imagination and identifying body parts; at age 2 years old, a child is capable of memory of two shapes and fine motor skills.

The inventor discovered that this development chart can be used as a guideline to identify the level of normalcy of a child, and in selecting a potential candidate patient child for medical treatment.

The inventor discovers that independent of age, intellect, disease states, if the child is able to function on any level at 18 to 24 months of age, either for the verbal or the non-verbal development, medical treatment in combination with physical and language training dramatically improves the child's language ability and later development.

Knowing that an average 2 year old has a vocabulary of between 50 and 300 words using 2 words together, an indication of a level of brain normal functioning, the medication will therefore enhance the frontal lobe to restore function to at least begin to hear these children vocalizing consonants, vowels, imitate the instructor, not just spontaneous but in response to the stimulus provided by the instructor. Using the developmental parameters at the nonverbal left side of the graph, the inventor was able to predict more likely than not would respond to the medication treatment with a dopamine agonist.

The nonverbal milestones can include receptive abilities', the ability of the infant to appropriately respond to changes in facial expressions of parents, to share experiences with their caregivers not to just make demands—between the ages of 7 and 12 months of age to be able to see or to be told by the parents that the infant was establishing joint attention.

For example; the infant beginning at 7 months, independent of whether or not they are keeping up with the appropriate vocalizations, begin to be able to focus not only on the parent but eye gaze to parent, to the desired object and than returning eye gaze to the parent is an example of a 7-12 month old evidencing the theory of mind, sharing information, an experience with their caregiver, not just demanding their time.

Assessment of the verbal ability of a subject can include but is not limited to measures of all the domains described herein: nonspeech oral-motor, speech production, prosody, voice, speech perception, language, and, for older children, linguistic/literacy skills. Of these, (a) inconsistent errors on consonants and vowels in repeated productions of syllables or words, (b) lengthened and disrupted coarticulatory transitions between sounds and syllables, (c) inappropriate prosody, especially in the realization of lexical or phrasal stress; (d) the inability to see a new word and to have the ability to identify and sequence in time and space the sounds not only by themselves but in relationship to one another to be able to produce to transform from a symbol, orthographic to sound representation but to do it according to the rules of language knowing where to divide the written symbols into units; (e) the inability to not only transform into sounds, but sounds in relationship in terms of speed and volume to have that word in the context have that meaning that the author of the written word wanted to convey. The cultural and linguistic background of each subject may optionally be assessed.

Metrics for quantitative assessment of the language ability include words per minute, three minute reading test, sentence complexity such as length in words, complexity of construction, etc. The number of correctly read syllables minuses the number of mistakes divided by the months of reading training may be used to assess the language ability development.

When treating a child who is incapable of communication, the child is tested about its language skills as well as visual-spatial comprehension skills. For example, a child may be asked to pronounce a few single syllable words, such as "ma, ma" "ba, ba" or to described a picture or read a few words. At the same time, the child's body motions and emotional interactions with other people are observed. If the child demonstrates a non-verbal age of at least 18 to 24 months, he or she may be capable of responding to medical intervention, a dopamine agonist to restore speech.

The medical intervention can be applied to children who are present on the apaxia pyramid, apraxia of speech and language who are at a minimum of 3 years of age and older having a demonstrable nonverbal mental age of between 18 and 24 months, independent of any and all medical conditions inclusive but not limited to speech and language delay, mental retardation, autism, autistic spectrum disorders, dyslexia, chromosomal disorders, muscular dystrophy, cerebral palsy.

This is achieved by administering drugs enhancing the concentrating of dopamine, such as methylphenidate, dexamphetamine, in any of their formulations independent of immediate or slow release, independent of how the compound was created, tablet, gel, suspension, etc.

The assessment methods may include performance in multiple contexts (e.g., spontaneous, elicited, imitation; syllable, single-word, phrase, sentence, discourse). Known tests such as Apraxia Profile, Screening Test of Developmental Apraxia of Speech-2 and Verbal Motor Production Assessment for Children may be combined in assessment of the left brain hemisphere and the right brain hemisphere development.

There is no age limitation for this treatment method, but generally patients are children of 2 to 12 years age.

The treatment methods thus comprise administering dopamine agonist medicine, such as methylphenidate (Ritalin, MPH, MPD), Dexedrine, to a selected patient. The term "administer" and "administering" are used to mean introducing a therapeutic substance into the subject. The therapeutic administration of a substance serves to attenuate any symptom or prevent additional symptoms or causative events from arising.

Dopamine, a neurotransmitter, plays a role in feelings of pleasure and is naturally released in rewarding experiences. Neuroimaging studies of medication-free depressed patients have found that depressed subjects have a functional deficiency of synaptic dopamine. Dopamine decreases "background firing" rates and increases the signal to noise ratio in target neurons by increasing dopamine levels in the brain. As a result, the drug may improve synaptic interactions and communications between synapses.

Forms of methylphenidate may include but not limited to dexmethylphenidate (Focalin), levomethylphenidate, and (racemic) dextro-, levomethylphenidate (Ritalin). Methylphenidate is a chain substituted amphetamine derivative that primarily acts as a norepinephrine-dopamine reuptake inhibitor. Methylphenidate is most active at modulating levels of dopamine and to a lesser extent noradrenaline. Key targets of methylphenidate are the dopamine transporter (DAT) and noradrenaline transporter (NET). MPH binds to and blocks DAT and NET, inhibiting the transport of the transporters' respective substrates. MPH may also act as a releasing agent by increasing the release of dopamine and norepinephrine.

Dextroamphetamine is also a psychostimulant drug which is known to produce increased wakefulness and focus as well as decreased fatigue and decreased appetite. Dextroamphetamine is the dextrorotatory, or "right-handed", stereoisomer of the amphetamine molecule. Names for dextroamphetamine include d-amphetamine, dexamphetamine, dexamfetamine, and (S)-(+)-amphetamine, with brand names to include Dexedrine and Dextrostat, and in some countries it is sold simply as Dexamphetamine Sulphate.

Dextroamphetamine administration increases the activity of the phosphoinositol cycle via an indirect release of dopamine and Norepinephrine. Because dextroamphetamine is a substrate analog at monoamine transporters, at all doses, dextroamphetamine prevents the re-uptake of these neurotransmitters by competing with endogenous monoamines for uptake. Transporter inhibition causes monoamines to remain in the synaptic cleft for a prolonged period. The drug can trigger direct release of norepinephrine and dopamine from the cytoplasmic transmitter pool, i.e. norepinephrine and dopamine efflux via transporter proteins, functionally reversing transporter action, which triggers a cascading release of catecholamines. This inversion leads to a release of large amounts of these neurotransmitters from the cytoplasm of the pre-synaptic neuron into the synapse, causing increased stimulation of post-synaptic receptors.

In addition, dextroamphetamine increases dopamine release in the prefrontal cortex; activation of the dopamine-2 receptors inhibits glutamate release in the prefrontal cortex. Activation of the dopamine-1 receptors in the prefrontal cortex, however, results in elevated glutamate levels in the nucleus accumbens which in turn increase locomotor activity.

As used herein and unless otherwise indicated, the phrase "therapeutically effective amount" (or "pharmaceutically effective amount") is measured by the therapeutic effectiveness of the substance. In one embodiment, the term "therapeutically effective amount" means an amount of a substance that is sufficient to provide the desired local or systemic effect and performance at a reasonable benefit/risk ratio attending any medical treatment. The response to the therapeutically effective amount may be a cellular, organ or tissue-specific response, or system or systemic response. In one embodiment, the phrase "therapeutically effective amount" of an administered substance is measured by the therapeutic effectiveness of the substance to improve language learning ability.

The same parameters used to diagnose the subject as having an apraxia-related disorder may be used to determine if the subject is demonstrating any type of "improvement" or lessening of symptoms. For example, an improvement in a subject may include but is not limited to, an increase in the number of correct phonemes when speaking, a more normal time spent enunciating words, the number of times the last consonant of a word is used correctly, the proper sequencing of words and events, appropriate sound intensity.

Depending where the patient is on the apraxia pyramid, for example vocalization, words, prosody, the number of words in the sentence, the number of types of words in the sentence, the grammar syntax, prosody, measuring the child to his/her previous ability 20-30 minutes ago in addition to medication. Unlike treatment of ADHD, the restoring function and opening therapeutic pathways is long lasting after half life of the medicine.

Dosages of these therapeutic drugs can vary between a broad limits, depending upon the severity of disorder being treated, the age and condition of the individual to be treated, etc. A physician will ultimately determine appropriate dosages to be used. In one embodiment, MPH, Dexedrine or is administered in a single dose. In another embodiment, MPH, Dexedrine is administered in multiple doses. For example, in one specific embodiment, dosage is administered orally either once or in multiple doses at a dose of about 2.5 mg per dose. In another specific embodiment, MPH, Dexedrine or Gabapentin is administered orally either once or in multiple doses at a dose of about 5 mg per dose. In another specific embodiment, MPH, Dexedrine or Gabapentin is administered orally either once or in multiple doses at a dose of about 7.5 mg per dose. In one specific embodiment, MPH, Dexedrine or Gabapentin is administered orally either once or in multiple doses at a dose of about 10 mg per dose MPH, Dexedrine or Gabapentin may be administered in long-term, including but not limited to the life of the subject. In another embodiment, the MPH, Dexedrine or Gabapentin is administered until the symptoms of the apraxia-related disorder have subsided or are reduced.

The examples herein are meant to illustrate only select embodiments of the present invention and are not intended to limit the scope of the inventive subject matter described herein. Any combination of any two or more of any of the embodiments described herein are contemplated.

EXAMPLES

Example 1

An 11 year autistic boy whose speech consisted of the spontaneous 2 word-3 words, whose volitional response was at best rarely 1 words, mostly of the tone unintelligible, whose ability to imitate sounds was limited to occasionally repeating ma, ma after instructor. This was his best after approximately 8 years of special education services inclusive of speech and language. at the time of examination he was being taught sign language as the sole means of communication.

The 11 year old was determined to have a mental age equal to that of a 2 year old recognizing that 2 year olds have a vocabulary of between 50 and 300 words, use 2 words together, and have intelligible speech 25% of the time.

Thirty minutes after receiving 10 mg tablets of methylphenidate he was recorded (with the parents permission) before and after being given imitating the following sounds, words, and sentences in response. He was able to imitate "ma ma ma", when shown a toy car and asked to repeat "car" after he was able to repeat "car"; when he was shown a bottle of water, he was able to express "daad, i wannnnnt waa tter", a conversation with his father. This was an 11 year old whose sole means of communication being offered him was sign language.

Example 2

A three and half year old boy was under early intervention for a year. He was able to make normal eye contacts, but was unable to follow instruction in saying single syllables such as "ma" "ma". The boy was determined to have a better than 24 month stage of nonverbal development, but less than 12 months development stage of verbal development. He was administered with one dosage of 5 mg of methylphenidate.

Half an hour later, this boy was able to follow instructions to mimic the sounds "ma" "ma" "ga" "ga".

Example 3

An eight year old boy with normal facial expressions, but was having difficult in school and was under special aid program. He was able to answer questions as to "what is your name", "how old are you", "what is your mama's name" and to describe school activities in simple sequence. But when he was asked to describe the books he read in class, he was unable to describe any content of any books. Instead he described what actions the book had. He could not give one example of the stories taught in the class. He was determined to have a good non-verbal development, but impaired verbal development. The boy was administered 5 mg of Dexedrine.

Half an hour later, the boy was able to state in sequence what he did in school with some details, and was able to describe a story about Abraham Lincoln and George Washington. He was also able to tell the difference of the word "compare" versus "contrast", answer questions as to the differences between Abraham Lincoln and George Washington.

Example 4

An eight year old boy, third grade in school, but was not doing well in school. He was diagnosed of having speech and language learning disabilities. He was able to follow instructions and answer questions as to "what is your name", but could not tell his mother's name and his relation to his baby brother. He could state what he did in the morning in school, but could not describe the content of a class. He was determined to have a good non-verbal development, but impaired verbal development. The boy was administered 5 mg of Dexedrine.

Half an hour later, he was able to describe the content of his mathematic class, answer with some details about what he read in the class, the plants and moths. Etc.

Example 5

A nine year old boy was diagnosed with dyslexia, was bale to make body motions and eye contacts. But he appeared not to understand questions. When he was asked to describe a picture, he gestured with his fingers to point to the picture, but could not describe the picture with words. His reading of a sentence was not intelligible. The boy was determined to have a good non-verbal development but impaired verbal development. He was administered with 10 mg of methylphenidate.

Half an hour later, this boy was able to read a sentence with smooth pronunciations, and the reading was smooth even with new words.

Example 6

A twelve year old boy was able to answer questions as to age, school name, what he did in the class. But he was not able to describe the content of the math class, unable to provide an example of what he did. He described the actions of reading a book, watching a movie, but unable to describe the content of a book or a class. The boy was determined to have a good level of non-verbal development, but impaired verbal development. He was administered 10 mg of Dexedrine.

Half an hour later, the boy was able to describe the content of his English lass and the sections of the class learned with some details. He also was able to tell the story of Christopher Columbus with some details, and answer questions with logic and reasoning as to how to use a compos to travel the globe.

Example 7

A two year and seven month old girl having chromosome 15 duplication was unable to make any sounds, or understand any instruction. She was diagnosed as autism or mental retardation. But she was able to hold a pen with correct hand gestures, and was able to bodily interact with her mother. She was determined to have at least 2 years old of nonverbal development, but less than 6 month verbal development. The girl was administered with a 2.5 mg of methylphenidate.

Thirty minutes later, the girl was able to make sounds of "ma mi", mimic "bye", "bye" and babble with sounds.

She was administered 2.5 mg of methylphenidate a day for two to three months. The follow up on her showed good progress in speaking sounds.

Example 8

An 11 years old girl who could not talk and walk after 10 years of speech therapy was only able to repeat "ba ba," la la" and two words in Spanish. She was able to wave hands and clapping, albeit with right elbow in fixed gesture. Her non-verbal and verbal development was about 2 years old.

After 30 minutes of treatment with a 5 mg of methylphenidate, she was able to repeat two syllable words, and was able to say "love you" and able to use her leg to stomped and sense the floor when hold to walk.

Figure 2:
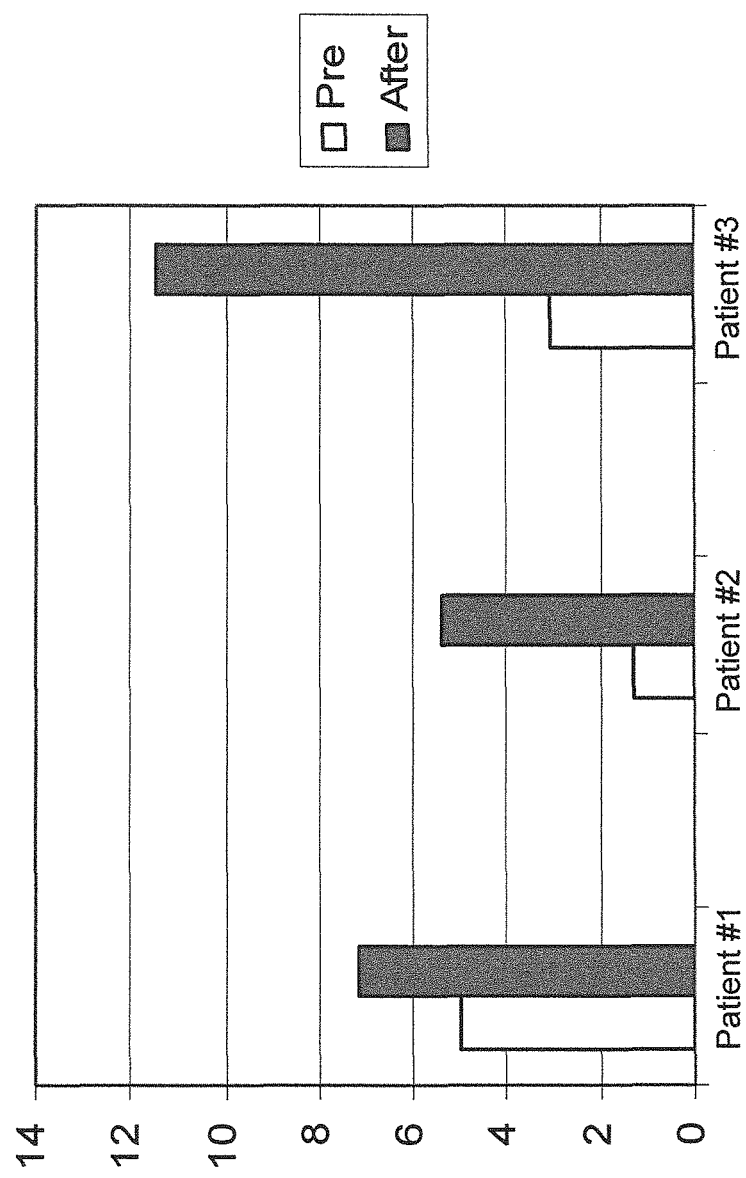
FIG. 2 is a comparison of the reading abilities of a group of children with a various diagnosed symptoms between pre-treatment and after-treatment with one dosage of 5-7.5 mg of methylphenidate.
Figure 3:
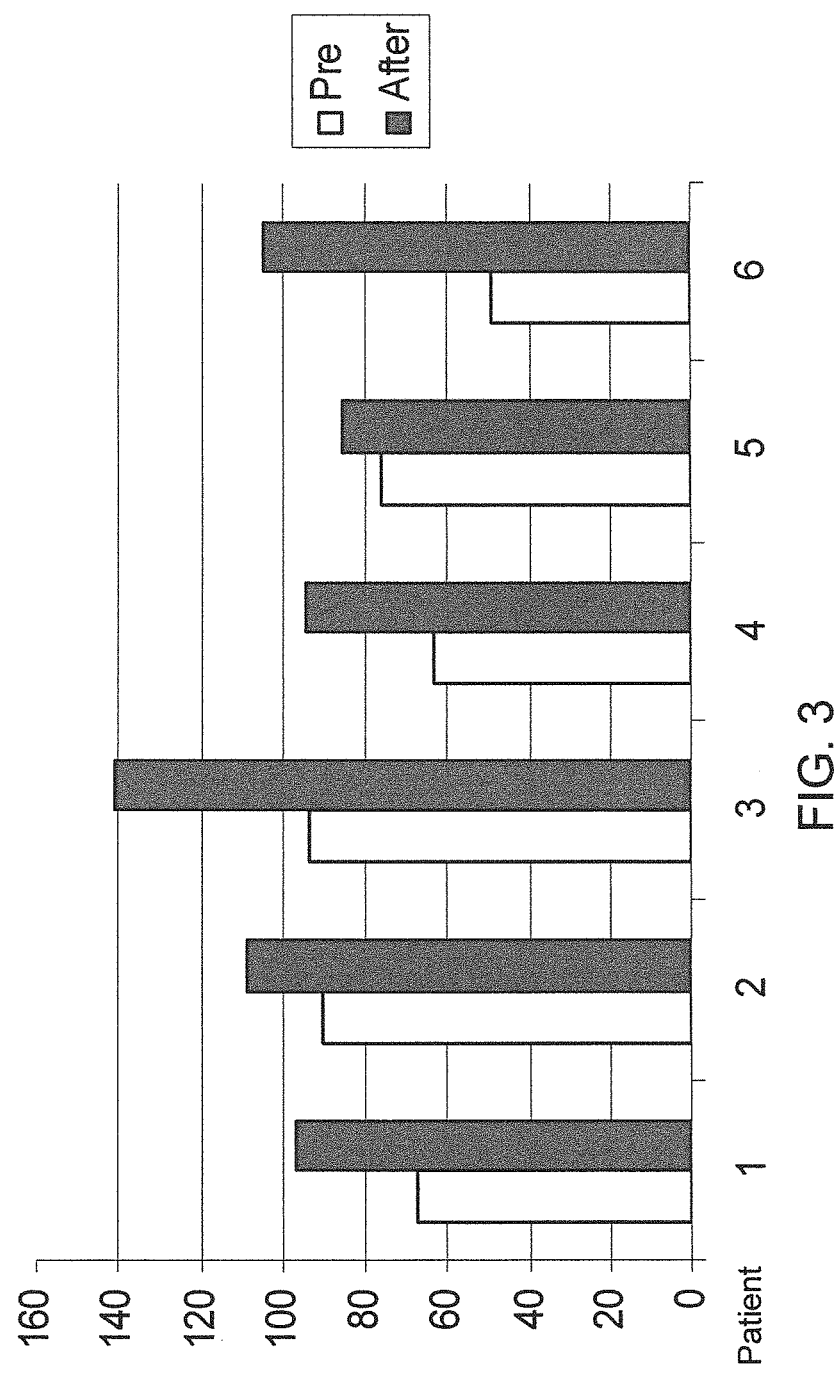
FIG. 3 is a comparison of the reading abilities of another group of children with a various diagnosed symptoms between pre-treatment and after-treatment with one dosage of 5-7.5 mg of methylphenidate.

In reference to FIG. 2 and FIG. 3. A total of nine children who had a good level of nonverbal development, but were not functioning well with reading and language skills were administered with 5 mg of methylphenidate. They were tested for three minute reading before and after administering the medicine. The mistakes in pronouncing syllables were counted. The correct pronunciation ratios (divided by the total number of syllables read) were compared between the pre-administering the drug and after administering the drug. All nine kids showed some improvement, varying from 11% to 300% improvement. Most of them had least 40% improvement.

It will be understood that in determining a developmental age of a child of approximately 18 to 24 months of age, a complementary determination includes, but is not limited to the following queries:

a. Is the child able to speak between 50-300 words of which 25% are intelligible?
b. Is the child able to identify 10 body parts upon inquiry?
c. Has the child developed imaginary play?
d. Is the child able to pick up a drawing instrument about a mid-section and make markings with the same upon paper?
e. Is the child able to demonstrate a theory of mind as determined by a professional diagnostician?

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

None of the description in the present application should be read as implying that any particular element, step, or function is an essential element which must be included in the claim scope: the scope of patented subject matter is defined only by the allowed claims. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A method for treating an apraxia of speech in a child, said method comprises:
    (a) determining that the child has an apraxia of speech comprising nonverbal development;
    (b) determining that the child has a cognitive development of at least 18-24 months;
    (c) administering a therapeutically effective dose of a dopamine agonist to the child, said dopamine agonist efficaciously affecting the apraxia effecting verbal development and wherein the dopamine agonist comprises a methylphenidate;
    whereby there is verbal development and the apraxia of speech is diminished.

2. The method of claim 1, wherein the nonverbal development comprises unintelligible speech.

3. The method of claim 1, wherein after step (c) the verbal development comprises intelligible speech.

4. A method for treating an apraxia of speech in a child, said method comprises:
    (a) determining that the child has an apraxia of speech comprising nonverbal development;
    (b) determining that the child has a cognitive development of at least 18-24 months;
    (c) administering a therapeutically effective dose of a dopamine agonist comprising a methylphenidate to the child;
    whereby there is verbal development and the apraxia of speech is diminished.

5. The method of claim 4, wherein verbal development prior to step (c) comprises limited verbal development consisting of several words or syllables.

6. The method of claim 1, wherein verbal development prior to step (c) comprises limited verbal development consisting of several words or syllables.

7. The method of claim 1, wherein the dopamine agonist comprises an analog of methylphenidate.

8. A method for treating an apraxia of speech in a child in need of such treatment, said method comprises;
    (a) administering an analog of methylphenidate to the child, efficaciously affecting the apraxia effecting verbal development; whereby the apraxia of speech is diminished and the verbal development improved.

9. The method of claim 8, wherein the verbal development prior to step (a) comprises limited verbal development consisting of several words or syllables.

* * * * *